United States Patent [19]
Slater et al.

[11] Patent Number: 5,591,202
[45] Date of Patent: Jan. 7, 1997

[54] ENDOSCOPIC INSTRUMENTS HAVING LOW FRICTION SHEATH

[75] Inventors: Charles R. Slater, Fort Lauderdale; Kevin W. Smith, Coral Gables; Matthew A. Palmer, Miami; Anthony I. Mazzeo, Ft. Lauderdale; George Nunez, Miami, all of Fla.

[73] Assignee: Symbiosis Corporation, Miami, Fla.

[21] Appl. No.: 234,641

[22] Filed: Apr. 28, 1994

[51] Int. Cl.⁶ .......................... A61B 17/00; A61B 10/00
[52] U.S. Cl. .................. 606/205; 606/170; 606/174; 128/751
[58] Field of Search .................. 606/51, 52, 174, 606/205, 206–211, 170; 128/750–755, 4, 6; 604/280

[56] References Cited

U.S. PATENT DOCUMENTS

| | | |
|---|---|---|
| 825,829 | 7/1906 | Heath . |
| 3,459,187 | 8/1969 | Pallotta . |
| 3,895,636 | 7/1975 | Schmidt . |
| 3,911,766 | 10/1975 | Fridolph . |
| 3,921,640 | 11/1975 | Freeborn . |
| 4,178,810 | 12/1979 | Takahashi . |
| 4,200,111 | 4/1980 | Harris . |
| 4,424,998 | 1/1984 | Lile . |
| 4,632,110 | 12/1986 | Sanagi . |
| 4,636,201 | 1/1987 | Ambrose . |
| 4,646,751 | 3/1987 | Maslanka . |
| 4,669,471 | 6/1987 | Hayashi . |
| 4,676,249 | 6/1987 | Arenas . |
| 4,721,116 | 1/1988 | Schintgen . |
| 4,763,668 | 8/1988 | Macek . |
| 4,815,460 | 3/1989 | Porat . |
| 4,815,476 | 3/1989 | Clossick . |
| 4,817,630 | 4/1989 | Schintgen . |
| 4,880,015 | 11/1989 | Nierman . |
| 4,887,612 | 12/1989 | Esser . |
| 4,889,118 | 12/1989 | Schwiegerling . |
| 4,936,312 | 6/1990 | Tsukagoshi . |
| 4,945,920 | 8/1990 | Clossick . |
| 5,035,248 | 7/1991 | Zinnecker . |

*Primary Examiner*—Michael Powell Buiz
*Assistant Examiner*—William Lewis
*Attorney, Agent, or Firm*—David P. Gordon

[57] ABSTRACT

A low friction sheath for endoscopic instruments is made from an extrusion grade of high density polyethylene (HDPE). The sheath is formed as an extruded polyethylene tube having an inner diameter slightly smaller than the outer diameter of the instrument it will cover. In order to place the sheath over the instrument, a containment sleeve is placed over the sheath and a source of pressurized gas is coupled to one end of the sheath. The endoscopic instrument tube is sealed and inserted into the other end of the sheath. The polyethylene sheath is filled with gas so that it expands against the containment sleeve and the endoscopic instrument tube is pushed into the expanded polyethylene sheath. The gas is released from the polyethylene sheath and it contracts against the outer surface of the endoscopic instrument tube. The sheath is preferably made from a HDPE having a microfractured surface with 10–20 micron fractures.

15 Claims, 2 Drawing Sheets

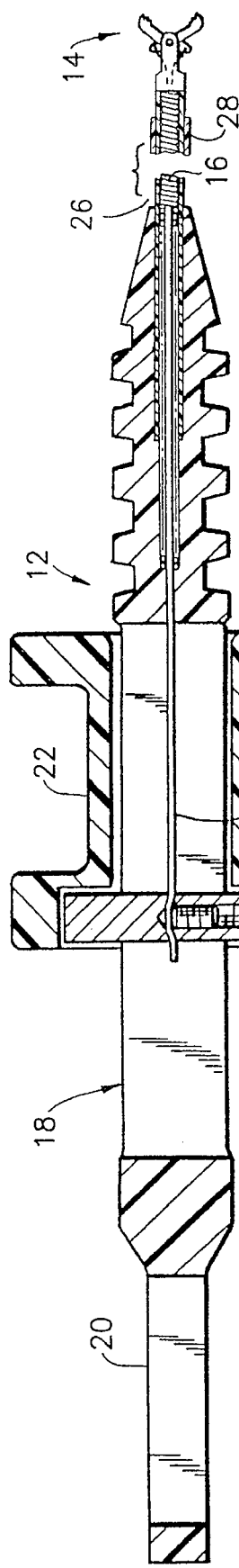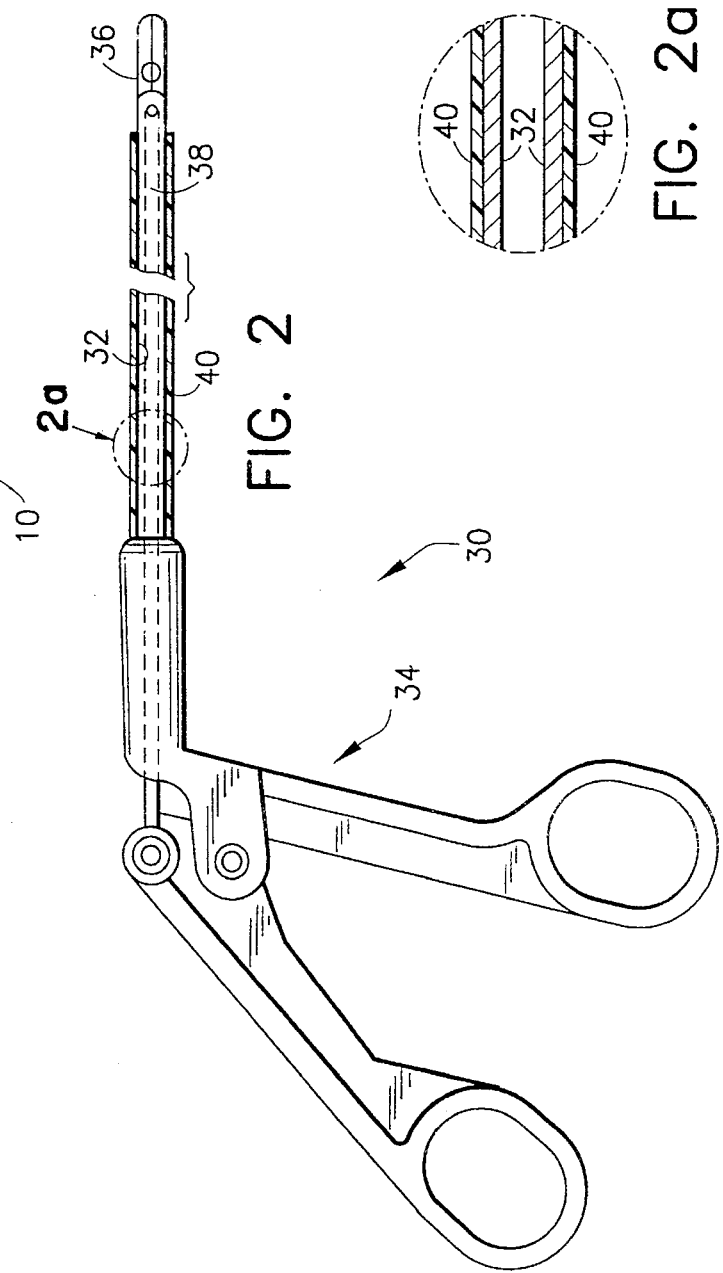

ENDOSCOPIC INSTRUMENTS HAVING LOW FRICTION SHEATH

BACKGROUND OF THE INVENTION

1. Field of the Invention

The invention relates to endoscopic instruments. More particularly, the invention relates to a low friction sheath for an endoscopic instrument such as an endoscopic biopsy forceps.

2. State of the Art

Endoscopic biopsy forceps generally include a relatively long (several feet) hollow flexible member (typically a coil) with one or more flexible control members extending therethrough. The proximal ends of the hollow member and the control members are coupled to a manual actuation device for imparting reciprocal axial movement of the control members relative to the hollow member. The distal end of the hollow member is coupled to a clevis upon which a pair of biopsy forceps jaws are rotatably mounted. The distal ends of the control members are coupled to the jaws so that axial movement of the control members relative to the hollow member causes the jaws to open or close. The endoscopic biopsy forceps typically are delivered to the biopsy site through an endoscope.

An endoscope has a relatively long flexible tube carrying fiber optics and a relatively narrow lumen through which the endoscopic biopsy forceps may be inserted. The practitioner guides the distal end of the endoscope to the biopsy site and uses the fiber optics to view the site. When the distal end of the endoscope is near the biopsy site, the practitioner inserts the biopsy forceps jaws into the narrow lumen of the endoscope and pushes the long hollow flexible member through the lumen until the jaws exit the distal end of the endoscope. Since the lumen of the endoscope is narrow and the endoscope typically takes a tortuous path to the biopsy site, it is often difficult to push the biopsy forceps through the lumen to the biopsy site. Thus, the design of endoscopic biopsy forceps is often concerned with reducing friction between the outer surface of the hollow flexible member of the forceps and the interior surface of the lumen of the endoscope. For example, it is now common to provide the hollow flexible member with a shrink wrapped "TEFLON" sheath along its entire length. Such a "TEFLON" sheath is also useful for electrically insulating the hollow flexible member when the forceps are made "hot" for electrocautery.

Other endoscopic tools are often provided with a similar shrink wrapped "TEFLON" sheath for electrical insulation and/or for decreasing friction on the outer surface of the tool. "TEFLON" has been considered the ideal material for these purposes because of its high lubricity and electrical insulating properties. However, "TEFLON" is relatively expensive. Since many endoscopic instruments are made to be disposable for safety reasons, the cost of providing a "TEFLON" sheath can become significant.

SUMMARY OF THE INVENTION

It is therefore an object of the invention to provide a low friction sheath for endoscopic instruments.

It is also an object of the invention to provide a low friction sheath for endoscopic instruments which has good electrical insulating properties.

It is another object of the invention to provide a method for applying a low cost lubricious electrically insulating sheath to an endoscopic instrument, in particular to an endoscopic biopsy forceps.

In accord with these objects which will be discussed in detail below, the endoscopic instrument of the invention is provided with a low friction sheath made from polyethylene. Typically, the polyethylene is an extrusion grade high density polyethylene (HDPE), although heat shrinkable or blow-molding grade HDPE can be utilized. Likewise, the low friction sheath can be made from a mixture of HDPE and low density polyethylene (LDPE). Regardless, the sheath is formed as an extruded tube of polyethylene having an inner diameter slightly smaller than the outer diameter of the tube it will cover. The polyethylene sheath according to the invention is preferably more lubricious than an FEP such as "TEFLON". Significantly, the low friction polyethylene sheath is only a small fraction of the cost of a FEP sheath of the same dimensions. The sheath of the invention is electrically resistive making it a good insulator for endoscopic instruments incorporating electrocautery functions. While HDPE and HDPE/LDPE mixed sheaths do not have the same heat resistance properties as FEP, it has been found to be adequate for almost all endoscopic applications. In situations where cautery significantly raises the ambient temperature at the distal end of the instrument, a short FEP sheath can be applied adjacent the distal end of the instrument while maintaining the HDPE or HDPE/LDPE mixture sheath on the remaining portions of the instrument.

In accord with the preferred method of the invention, the polyethylene sheath is placed in a containment sleeve, and a source of pressurized gas is coupled to one end of the tube. The tube or coil of the endoscopic instrument is filled with a stiffening wire and is inserted into the other end of the polyethylene sheath. The polyethylene sheath is filled with gas so that it expands against the containment sleeve and the tube of the endoscopic instrument with the wire contained therein is pushed into the expanded polyethylene sheath. The gas is then released from the polyethylene sheath (i.e. the pressure is reduced) and the polyethylene sheath contracts against the outer surface of the tube of the endoscopic instrument. A silicone based lubricant may then be applied to the outer surface of the sheath. Alternatively, a silicon based lubricant can be mixed with the polyethylene prior to extrusion of the polyethylene sheath. The lubricant adheres to the fractured surface of the polyethylene in contrast to the smooth surface of TEFLON, which repels lubricant.

Additional objects and advantages of the invention will become apparent to those skilled in the art upon reference to the detailed description taken in conjunction with the provided figures.

BRIEF DESCRIPTION OF THE DRAWINGS

FIG. 1 is a broken side elevation view in partial section of an endoscopic biopsy forceps having a low friction sheath according to the invention;

FIG. 2 is a broken side elevation view in partial section of a disposable endoscopic surgical instrument having a low friction sheath according to the invention;

FIG. 2a is an enlarged view of a portion of FIG. 2 as indicated by the arrow leading from FIG. 2a to FIG. 2;

DETAILED DESCRIPTION OF THE PREFERRED EMBODIMENTS

Figure 3:
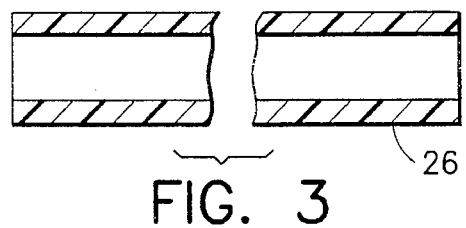
FIG. 3 is an enlarged broken longitudinal cross sectional view of an HDPE tube used for creating the low friction sheath of the invention.

FIG. 1 shows an endoscopic biopsy forceps 10 having a proximal handle 12, a pair of distal jaws 14, and a long flexible coil 16 connecting the jaws to the handle. The handle 12 includes a slotted shaft 18 having a thumb ring 20 and a displaceable spool 22. A pair of pull wires 24 coupled to the spool 22 extend through the coil 16 and are coupled to the jaws 14. Relative movement of the spool and the thumb ring causes opening and closing of the jaws. According to the invention, a low friction polyethylene sheath 26 is provided on the outer surface of the coil 16 along substantially all of its length. As mentioned above, if the biopsy forceps 10 are provided with cautery capability, a short length of TEFLON sheath 28 is preferably provided at the distal end of the coil 16, proximal of the jaws 14 so that the polyethylene sheath 26 is not exposed to the high temperatures generated by cautery at the jaws 14.

The lubricious, low friction polyethylene sheath of the invention can also be provided on other types of endoscopic tools where a "TEFLON" sheath is presently used. For example, the endoscopic surgical instrument 30 shown in FIGS. 2 and 2a generally includes a hollow tube 32 having a manual actuator 34 coupled to its proximal end and a pair of end effectors 36 mounted at its distal end. A push rod 38 extends through the tube 32 and is coupled at its proximal end to the actuator 34 and at its distal end to the end effectors 36. Manipulation of the actuator 34 causes reciprocal movement of the push rod 38 through the tube 32 to open and close the end effectors 36. According to the invention the outer surface of the tube 32 is provided with a low friction polyethylene sheath 40 along substantially its entire length. As with the biopsy forceps described above, if cautery capability is provided in the instrument 30, the distal portion of the tube 32 is preferably covered with a short length of TEFLON sheath.

Figure 4:
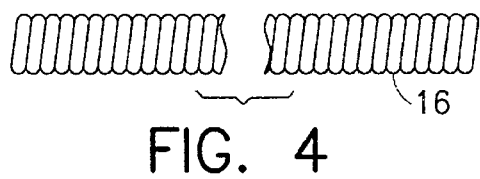
FIG. 4 is an enlarged broken side elevation view of an endoscopic biopsy forceps coil prior to application of the low friction sheath according to the invention.

Turning now to FIGS. 3–7, the polyethylene sheath according to the invention is preferably made from an extrusion grade HDPE (such as FINA-7740), although a blow-molding grade can be utilized, particularly if gels in the blow-molding grade HDPE are filtered out. In some applications, however, it may be desirable to blend 75% HDPE with 25% LDPE which gives the resulting mixture a bit more elasticity without severely compromising its lubricity. If desired, additional lubricity can be gained by adding lubricant directly to the HDPE or HDPE/LDPE mixture prior to extrusion. Regardless, the HDPE or HDPE/LDPE mixture is extruded to form a tube or sheath 26 as shown in FIG. 3. The polyethylene sheath 26 is preferably long enough to cover the component to which the sheath will be applied, for example biopsy forceps coil 16 as shown in FIG. 4. Moreover, the internal diameter of the polyethylene sheath 26 is preferably slightly smaller than the external diameter of the coil 16.

Figure 5:
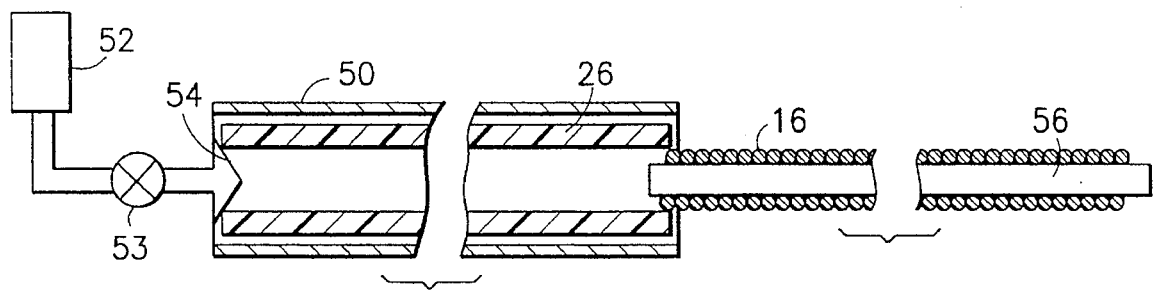
FIG. 5 is an enlarged broken longitudinal cross sectional view of an HDPE tube located within a containment sleeve with a source of pressurized gas coupled to one end and a stiffened endoscopic biopsy forceps coil partially inserted in the other end.
Figure 6:
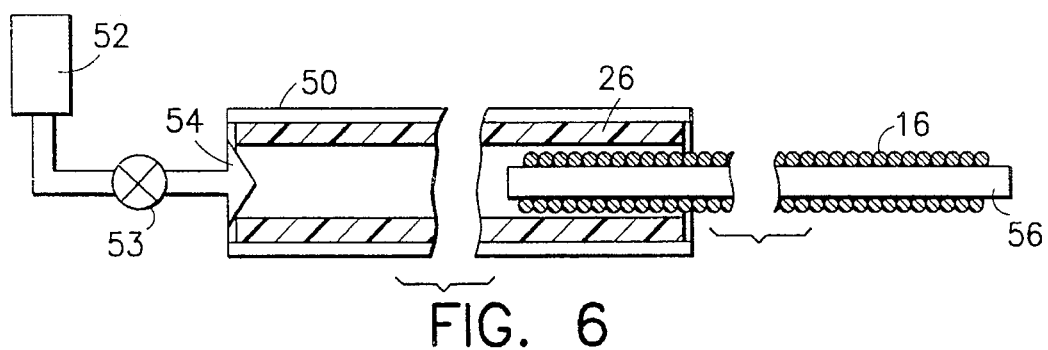
FIG. 6 is a view similar to FIG. 5 showing the tube expanded by gas and the stiffened coil pushed partially into the expanded tube.
Figure 7:
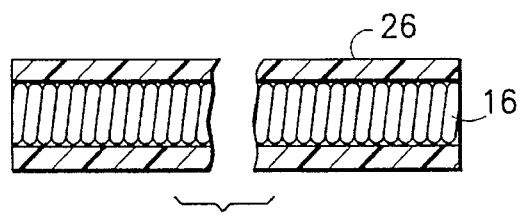
FIG. 7 is an enlarged broken side elevation view in partial section showing the endoscopic biopsy forceps coil with the compressed HDPE sheath covering its outer surface.

According to the method of the invention, the polyethylene sheath (tube) 26 is inserted into a containment sleeve 50. The containment sleeve 50 has an internal diameter which is slightly larger than the external diameter of the polyethylene sheath 26 and is preferably approximately slightly larger than the sum of the external diameters of the polyethylene sheath 26 and the coil 16 less the internal diameter of the polyethylene sheath 26. The containment sleeve 50 is preferably long enough to contain the entire polyethylene sheath 26. With the polyethylene sheath 26 inside the containment sleeve 50, a source of pressurized gas 52 is coupled to one end of the polyethylene sheath through a valve 53 and a fitting 54. A rigid member 56 is inserted into the coil 16 to stiffen the coil and to substantially seal its hollow interior. An end of the coil 16 is then inserted into the other end of the polyethylene tube 26 as shown in FIG. 5. Those skilled in the art will appreciate that since the external diameter of the coil is slightly larger than the internal diameter of the polyethylene tube, the coil cannot be fully inserted into the polyethylene tube. However, the elasticity of the polyethylene tube will allow enough diametrical expansion at the end of the polyethylene tube so that the end of the coil can "plug" the end of the polyethylene tube. After the coil has been inserted in this manner, the valve 53 is opened and pressurized gas enters the interior of the polyethylene tube through the fitting 54. The coil 16 with the rigid member 56 substantially prevents gas from escaping the interior of the polyethylene tube. The elasticity of the polyethylene tube yields to the pressure of the gas and the polyethylene tube expands diametrically until it is restrained by the interior of the containment sleeve 50. The coil 16 with rigid member 56 is then pushed freely into the polyethylene tube as shown in FIG. 6. When the coil is substantially covered by the polyethylene tube, the valve 53 is closed and the fitting 54 is removed from the polyethylene tube. The polyethylene tube contracts diametrically until it engages the exterior surface of the coil 16. The polyethylene tube-wrapped coil is removed from the retaining sleeve and the rigid member is removed from the coil. The flexibility of the coil is not significantly reduced by the polyethylene sheath 26 which now embraces the coil 16 as shown in FIG. 7. Moreover, as mentioned above, the sheath 26 has a highly lubricious outer surface and is electrically non-conductive.

Those skilled in the art will appreciate that the above-described method can be used to apply a sheath to any substantially cylindrical member such as the coil 16 or the tube 32 shown in FIGS. 2 and 2a. It will be appreciated that when the cylindrical member is substantially rigid such as the tube 32, it is not necessary to insert a rigid member 56 into the tube 32 before inserting the tube 32 into the polyethylene sheath. Rather, it is only necessary to plug the interior of the tube 32 to inhibit gas from escaping while the polyethylene sheath is being expanded. In addition, while no heating of the polyethylene sheath is required, the method can be carried out at elevated temperatures if desirable, for example at temperatures between 110° F. and 160° F. The heating of the polyethylene sheath prior to and/or during expansion, while not preferred, does aid in helping the polyethylene sheath expand as required by the method invention.

It is believed that the lubricity of the polyethylene tube of the invention is provided by the surface structure of the polyethylene which includes longitudinal microfractures of a desired width. The microfractured surface of the polyethylene sheath of the invention is believed to be more lubricious than the smooth FEP ("TEFLON") surface because the fractures reduce the outer surface contact area, thus decreasing surface tension. In addition, lubrication applied to the fractured surface of the polyethylene sheath tends to adhere to the surface because of the microfractures. Since it is believed that it is the microfractured surface of the polyethylene sheath which makes it so suitable for the uses described herein, it should be appreciated that materials other than polyethylene which exhibit a similarly microfractured surface may also be similarly useful for providing an endoscopic instrument sheath.

For excellent results, the width of the microfractures in the surface of the polyethylene tube are preferably between ten and twenty microns. However, polyethylene tubes with either smaller and larger characteristic microfractures can still provide surfaces which are more lubricious than FEP. It should be noted that for purposes herein, the term "lubricity" or "lubricious" relates to the lubricity of the outer surface of an endoscopic instrument vis-a-vis an endoscope through which the endoscopic instrument will pass. Typically, the endoscope surface past which the endoscopic instrument will travel is made from polytetrafluoroethylene (PTFE).

While the preferred embodiment of the invention utilizes extrusion grade HDPE which is fit over the coil or tube of an endoscopic instrument as discussed above with reference to FIGS. 3–7, according to another embodiment of the invention, a heat shrinkable grade HDPE can be utilized. If a heat shrinkable grade HDPE is utilized, the method of application is similar to where a FEP (e.g., "TEFLON") shrink-tubing is utilized; i.e., the tubing is placed over the instrument and heated until it shrinks and grabs the instrument.

There have been described and illustrated herein several embodiments of endoscopic instruments having low friction (lubricious) sheaths. While particular embodiments of the invention have been described, it is not intended that the invention be limited thereto, as it is intended that the invention be as broad in scope as the art will allow and that the specification be read likewise. Thus, while particular grades and densities of polyethylene have been disclosed, it will be appreciated that other grades and densities could be utilized. Also, while two exemplary endoscopic instruments have been shown, it will be recognized that other types of endoscopic instruments could be provided with the inventive sheath. Moreover, while particular configurations have been disclosed in reference to the apparatus used to perform the method of the invention, it will be appreciated that other configurations could be used as well. Furthermore, while the sheath has been disclosed as being made from polyethylene, it will be understood that different materials having the properties of the polyethylene described herein may achieve the same or similar function as disclosed herein. It will therefore be appreciated by those skilled in the art that yet other modifications could be made to the provided invention without deviating from its spirit and scope as so claimed.

We claim:

1. An endoscopic instrument comprising:
   a) a cylindrical member having a proximal end and a distal end;
   b) at least one end effector coupled to said distal end of said cylindrical member;
   c) handle means coupled to said proximal end of said cylindrical member; and
   d) a polyethylene sheath covering substantially all of said cylindrical member between said proximal and distal ends.

2. An endoscopic instrument according to claim 1, wherein:
   said polyethylene sheath comprises high density polyethylene.

3. An endoscopic instrument according to claim 2, wherein:
   said polyethylene sheath has a plurality of 10–20 micron fractures on its outer surface.

4. An endoscopic instrument according to claim 3, further comprising:
   a lubricant either in or on said polyethylene sheath.

5. An endoscopic instrument according to claim 2, wherein:
   said high density polyethylene is extrusion grade.

6. An endoscopic instrument according to claim 1, wherein:
   said polyethylene sheath comprises a mixture of high density polyethylene and low density polyethylene.

7. An endoscopic instrument according to claim 6, wherein:
   said high density polyethylene is one of blow-molding grade and heat shrinkable grade.

8. An endoscopic instrument according to claim 1, further comprising:
   a lubricant either in or on said polyethylene sheath.

9. An endoscopic instrument according to claim 1, further comprising:
   a fluorethylene polymer sheath at said distal end of said cylindrical member.

10. An endoscopic instrument according to claim 1, wherein:
    said cylindrical member is a metal coil.

11. An endoscopic instrument, comprising:
    a) a cylindrical member having a proximal end and a distal end;
    b) at least one end effector coupled to said distal end of said cylindrical member;
    c) handle means coupled to said proximal end of said cylindrical member; and
    d) a plastic sheath covering at least a portion of said cylindrical member between said proximal and distal ends, said plastic sheath having a microfractured outer surface,
       wherein said plastic sheath having a microfractured outer surface causes said endoscopic instrument to be more lubricious when passing through an endoscope than a similar endoscopic instrument covered with a fluorethylene polymer sheath.

12. An endoscopic instrument according to claim 11, wherein:
    said microfractured surface comprises a plurality of longitudinal fractures having a width of between ten and twenty microns.

13. An endoscopic instrument according to claim 11, further comprising:
    a lubricant either in or on said plastic sheath.

14. An endoscopic instrument according to claim 11, further comprising:
    a fluorethylene polymer sheath at said distal end of said cylindrical member.

15. An endoscopic instrument according to claim 11, wherein:
    said cylindrical member is a metal coil.

* * * * *